US006504019B2

(12) United States Patent
Yang et al.

(10) Patent No.: US 6,504,019 B2
(45) Date of Patent: Jan. 7, 2003

(54) NUCLEIC ACID PROBES HAVING HIGHLY HYDROPHILIC NON-NUCLEOSIDIC TAGS WITH MULTIPLE LABELS, AND USES THEREOF

(75) Inventors: Guohan Yang, Mansfield, MA (US); Donna M. Ford, Plainville, MA (US); Say-Jong Law, Westwood, MA (US); John E. Monahan, Walpole, MA (US); Todd B. Sells, Bellingham, MA (US)

(73) Assignee: Bayer Corporation, Medfield, MA (US)

( * ) Notice: Subject to any disclaimer, the term of this patent is extended or adjusted under 35 U.S.C. 154(b) by 0 days.

(21) Appl. No.: 09/813,644

(22) Filed: Mar. 21, 2001

(65) Prior Publication Data
US 2002/0015953 A1 Feb. 7, 2002

Related U.S. Application Data
(60) Provisional application No. 60/192,026, filed on Mar. 24, 2000.

(51) Int. Cl.$^7$ .................. C07H 21/04; C07H 21/02; C12A 1/68; C07D 413/00
(52) U.S. Cl. .................. 536/22.1; 536/23.1; 435/6; 544/83; 935/22; 935/28; 935/76
(58) Field of Search ............ 435/6; 536/22.1, 536/23.1; 544/83; 935/22, 28, 76

(56) References Cited

U.S. PATENT DOCUMENTS

| | | | |
|---|---|---|---|
| 4,914,210 A | 4/1990 | Levenson et al. | 548/413 |
| 4,997,928 A | 3/1991 | Hobbs, Jr. | 536/27 |
| 5,128,476 A | 7/1992 | Zhang et al. | 548/113 |
| 5,212,304 A | 5/1993 | Fung et al. | 544/157 |
| 5,245,022 A | 9/1993 | Weis et al. | 536/24.5 |
| 5,247,081 A | 9/1993 | Edge | 540/524 |
| 5,252,760 A | 10/1993 | Urdea et al. | 552/105 |
| 5,258,506 A | 11/1993 | Urdea et al. | 536/23.1 |
| 5,359,100 A | 10/1994 | Urdea et al. | 552/105 |
| 5,391,723 A | 2/1995 | Priest | 536/23.1 |
| 5,391,785 A | 2/1995 | Jones et al. | 552/105 |
| 5,420,330 A | 5/1995 | Brush | 558/185 |
| 5,451,463 A | 9/1995 | Nelson et al. | 428/402 |
| 5,656,731 A | 8/1997 | Urdea | 530/391.1 |
| 5,710,264 A | 1/1998 | Urdea et al. | 536/23.1 |

FOREIGN PATENT DOCUMENTS

| | | |
|---|---|---|
| DE | 4239531 | 5/1994 |
| EP | 0292128 | 11/1988 |
| JP | 63-290896 | 11/1988 |
| WO | WO 90/00622 | 1/1990 |
| WO | WO 90/09786 | 9/1990 |
| WO | WO 93/06122 | 4/1993 |
| WO | WO 93/20239 | 10/1993 |
| WO | WO 94/15620 | 7/1994 |

OTHER PUBLICATIONS

Chang et al., (1991), "Improved Methods for the Synthesis of Branched DNA (bDNA) for Use as Amplification Multimers in Bioassays," *Nucleosides & Necleotides* 10(1–3):389–392.

Fontanel et al. (1994), "Sterical Recognition By $T_4$ Polynucleotide Kinase of Non–nucleosidic Moieties 5'–attached to Oligonucleotides," *Nucleic Acids Research* 22(11):2022–2027.

Herve et al. (1991), "Phosphoramidite Reagents for the Easy Preparation of Polylabeled Oligonucleotide Probes," *Chemical Abstracts* 115:939.

Horn et al. (1986), "A Chemical 5'–Phosphorylation of Oligodeoxyribonucleotides that Can Be Monitored by Trityl Cation Release," *Tetrahedron Letters* 27(39):4705–4708.

Horn et al. (1989), "The Synthesis of Branched Oligonucleotides as Signal Amplification Multimers for Use in Nucleic Acid Assays," *Nucleosides & Nucleotides* 8(5 & 6):875–877.

Hudson et al. (1993), "Nucleic Acid Dendrimers: Novel Biopolymer Structures," *J. Am. Chem. Soc.* 115(6):2119–2124.

Igloi et al. (1994), "Oligoribonucleotide Reagent for Attaching Substances to Nucleic Acids, Method for Its Preparation, and Use of the Reagent," *Chemical Abstracts* 121:390–391.

Ma et al. (1993), "Design and Synthesis of RNA Miniduplexes Via a Synthetic Linker Approach," *Biochemistry* 32:1751–1758.

Newton et al. (1993), "The Production of PCR Products With 5' Single–stranded Tails Using Primers That Incorporate Novel Phosphoramidite Intermediates," *Nucleic Acids Research* 21(5):1155–1162.

Richardson et al. (1991), "Tethered Oligonucleotide Probes. A Strategy for the Recognition of Structured RNA," *J. Am. Chem. Soc.* 113(13):5109–5111.

Shchepinov et al. (1997), "Oligonucleotide Dendrimers: Synthesis and Use as Polylabelled DNA Probes," *Nucleic Acids Research* 25(22):4447–4454.

Teigelkamp et al. (1993), "Branched Poly–labelled Oligonucleotides: Enhanced Specificity of Fork–shaped Biotinylated Oligoribonucleotides for Antisense Affinity Selection," *Nucleic Acids Research* 21(19):4651–4652.

Primary Examiner—W. Gary Jones
Assistant Examiner—Arun K. Chakrabarti
(74) Attorney, Agent, or Firm—Dianne E. Reed; Reed & Associates

(57) ABSTRACT

Highly hydrophilic non-nucleosidic tags with multiple labels are provided for use in nucleic acid probes. The tags are branched structures having a phosphodiester backbone, which have the advantages of a small dimensional size and high hydrophilicity. After the tag is labeled, its high negative charge and minimal size help to keep the carriers away from DNA or RNA molecules, due to repulsion between negative charges. Non-specific intercalation and steric hindrance are therefore minimized, and the hydrophobicity, if any of reporter molecules is reduced. The probes are used in place of conventionally labeled oligonucleotides for a variety of hybridization reactions.

9 Claims, No Drawings

NUCLEIC ACID PROBES HAVING HIGHLY HYDROPHILIC NON-NUCLEOSIDIC TAGS WITH MULTIPLE LABELS, AND USES THEREOF

CROSS REFERENCE TO RELATED APPLICATION

This application claims priority to U.S. Provisional Application Serial No. 60/192,026, filed on Mar. 24, 2000.

INTRODUCTION

BACKGROUND

Nucleic acids are set apart from other biomolecules by their ability to hybridize to complementary sequences, a feature that is exploited in nature for the replication of genetic information. Hybridization specificity is exploited in research and diagnostics to generate information about the presence and quantity of nucleic acid sequences. Hybridization assays are generally based on the specific binding of a single stranded analyte to a labeled single stranded probe, followed by detection of the resulting duplexes. Variations of this basic scheme have been developed to enhance specificity, facilitate the separation of the duplexes from extraneous materials, and/or amplify the detectable signal.

The development of solid phase oligonucleotide synthesis has greatly simplified the production of specific nucleic acid probe and primers. Synthetic probes are widely used for all aspects of nucleic acid diagnosis, therapy and investigation. A feature that can be provided only in synthesized probes is comb-type branched multimers, which are composed of a linear backbone and pendant side chains. The backbone includes a segment that provides a specific hybridization site for a nucleic acid of interest, while the pendant side chains include iterations of a segment that provide specific hybridization sites to a second sequence of interest. The branch points are typically provided by protected phosphoramidites, as described in U.S. Pat. No. 5,359,100 (Urdea et al.); U.S. Pat. No. 5,656,731 (Urdea); U.S. Pat. No. 5,124,246 (Urdea et al.) and U.S. Pat. No. 5,710,264 (Urdea et al.), which are introduced during the oligonucleotide synthesis. The branch points may by symmetric or asymmetric.

An appealing aspect of synthetic primers is the ability to tag the probe as it is synthesized, thereby eliminating a separate labeling procedure. Common tags include internal or terminal tags or spacers, where an attached detectable label may be fluorescein or other fluorochromes, or a binding moiety such as biotin, digoxigenin, etc. Spacers known in the art include those with a 2-aminobutyl-1,3-propanediol backbone (U.S. Pat. No. 5,451,463), which is incorporated during phosphoramidite synthesis.

Detection of specific genetic sequences is an area of active research and development. 1X However, many problems still exist, such as low levels of signal, small sample size, high sample complexity, and the like. Improvements in the ability to provide a multiplicity of labels to a specific probe sequence are of interest, particularly using reagents that are compatible with standard phosphoramidite synthesis. The present invention addresses these issues.

RELEVANT LITERATURE

The synthesis of multiple-label carriers using DNA synthesis chemistry is disclosed in U.S. Pat. No. 5,359,100 (Urdea); European Patent EP 0 292 128 (Segev), and WO 90/00622 (Kwiatkowski et al.) The use of triethylene glycol as a building block is described in U.S. Pat. No. 4,914,210 (Leveason et al.) The basic method for solid phase DNA synthesis using phosphoramidite chemistry is described in U.S. Pat. No. 4.458,066, issued Jul. 3, 1984; U.S. Pat. No. 4,500,707, issued Feb. 19, 1985; and U.S. Pat. No. 5,153,319, issued Oct. 6, 1992. Reagents and protocols are widely available, for example from Applied Biosystems, Inc. (Foster City, Calif.). Branching phosphoramidites are commercially available, for example from Clontech (Palo Alto, Calif.).

SUMMARY OF THE INVENTION

Nucleic acid probes having highly hydrophilic non-nucleosidic tags with multiple labels are provided. The tags are branched structures synthesized using solid phase phosphoramidite chemistry, generally in combination with synthesis of the nucleic acid portion of the probe. The building blocks of the tag are protected glycerol, mono- and di-ethylene glycol phosphoramidites; and reagents that introduce attachment sites for labels. The resulting tag structure permits introduction of multiple labels, while enhancing the hydrophilicity of the probes through additional phosphodiester moieties.

DESCRIPTION OF THE PREFERRED EMBODIMENTS

DEFINITIONS

It is to be understood that this invention is not limited to the particular methodology, protocols, constructs, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a probe" includes a plurality of such probes and reference to "the structure" includes reference to one or more such structures and equivalents thereof known to those skilled in the art, and so forth. All technical and scientific terms used herein have the same meaning as commonly understood to one of ordinary skill in the art to which this invention belongs unless clearly indicated otherwise.

A probe refers to a biopolymer comprising a nucleic acid moiety and a tag moiety. A labeled probe further comprises one or more detectable label moieties covalently or non-covalently attached to the attachment sites provided by the tag moiety. The nucleic acid sequence is complementary to a nucleic acid sequence of interest present in a target analyte.

As used herein, the term target region or target nucleotide sequence refers to a probe binding region contained within the target molecule. The term target sequence refers to a sequence with which a probe will form a stable hybrid under desired conditions.

The nucleic acid moiety of the probe as used herein is conventional. The length, degeneracy, and specific sequence of the nucleic acid moiety is determined largely by the use for which it is intended. Generally the length of a particular strand will be sufficiently long to provide for specific hybridization of the sequence of interest, and sufficiently short to provide for a difference in hybridization between the sequence of interest and other sequences such as may be present in the sample. For example, detection of a single base change in a genetic sequence may be accomplished with probes of from about 12 to 25 nucleotides in length. Multiple strands may be combined in a comb or fork-like structure.

It will be appreciated that the binding sequences need not have perfect complementarity to provide stable hybrids. In many situations, stable hybrids will form where fewer than about 10% of the bases are mismatches, ignoring loops of four or more nucleotides. Accordingly, as used herein the term "complementary" refers to an oligonucleotide that forms a stable duplex with its "complement" under assay conditions, generally where there is about 90% or greater homology.

The nucleic acid moiety is typically synthesized in vitro using standard chemistry, and may be naturally occurring, e.g. DNA or RNA, or may be synthetic analogs, as known in the art. Such analogs may be preferred for use as probes because of superior stability under assay conditions. Modifications in the native structure, including alterations in the backbone, sugars or heterocyclic bases, have been shown to increase intracellular stability and binding affinity. Among useful changes in the backbone chemistry are phosphorothioates; phosphorodithioates, where both of the non-bridging oxygens are substituted with sulfur; phosphoramidites; alkyl phosphotriesters and boranophosphates. Achiral phosphate derivatives include 3'—O—5'—S-phosphorothioate, 3'–S—5'—O-phosphorothioate, 3'—CH$_2$—5'—O-phosphonate and 3'—NH—5'—O-phosphoroamidate. Peptide nucleic acids replace the entire ribose phosphodiester backbone with a peptide linkage.

Sugar modifications are also used to enhance stability and affinity. The a-anomer of deoxyribose may be used, where the base is inverted with respect to the natural b-anomer. The 2'—OH of the ribose sugar may be altered to form 2'—O-methyl or 2'—O-allyl sugars, which provides resistance to degradation without compromising affinity.

Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-Propynyl-2'-deoxyuridine and 5-propynyl-2'-deoxycytidine have been shown to increase affinity and biological activity when substituted for deoxythymidine and deoxycytidine, respectively.

These terms include double- and single-stranded DNA, as well as double- and single-stranded RNA, DNA:RNA hybrids, and hybrids between PNAs and DNA or RNA, and also include known types of modifications, for example, labels which are known in the art, methylation, "caps", those containing pendant moieties, such as, for example, proteins, including nucleases, toxins, antibodies, signal peptides, poly-L-lysine, etc., those with intercalators, e.g. acridine, psoralen, etc., those containing chelators, e.g. metals, radioactive metals, boron, oxidative metals, etc., those containing alkylators, those with modified linkages, e.g. alpha anomeric nucleic acids, etc., as well as unmodified forms of the polynucleotide or oligonucleotide.

The term polynucleotide analyte refers to a single- or double-stranded nucleic acid molecule that contains a target nucleotide sequence. The analyte nucleic acids may be from a variety of sources, e.g. biological fluids or solids, food stuffs, environmental materials, etc., and may be prepared for the hybridization analysis by a variety of means, e.g. proteinase K/SDS, chaotropic salts, or the like. The term "polynucleotide analyte" is used interchangeably herein with the terms "analyte," "analyte nucleic acid" and "target."

As used herein, a biological sample refers to a sample of tissue or fluid isolated from an individual, including but not limited to, for example, plasma, serum, spinal fluid, semen, lymph fluid, the external sections of the skin, respiratory, intestinal, and genitourinary tracts, tears, saliva, milk, blood cells, tumors, organs, and also samples of in vitro cell culture constituents, e.g. conditioned medium resulting from the growth of cells in cell culture medium, virus-infected cells, recombinant cells, and cell components. Exemplary uses of the subject probes are in detecting and/or quantitating: viral nucleic acids, such as from hepatitis B virus ("HBV"), hepatitis C virus ("HCV"), hepatitis D virus ("HDV"), human immunodeficiency virus ("HIV"), and the herpes family of viruses, including herpes zoster (chicken pox), herpes simplex virus I & II, cytomegalovirus, Epstein-Barr virus, Herpes VI virus; bacterial nucleic acids, such as Chlamydia, Mycobacterium, etc.; and numerous human sequences of interest.

The term nonspecific hybridization is used to refer to those occurrences in which a segment of a first polynucleotide which is intended to hybridize to a segment of a selected second polynucleotide also hybridizes to a third polynucleotide, triggering an erroneous result, i.e. giving rise to a situation where label may be detected in the absence of target analyte. The use of the term "hybridizes" is not meant to exclude non-Watson-Crick base pairing.

Nonspecific binding refers to those occurrences in which a polynucleotide binds to a solid support, or other assay component, through an interaction, which may be either direct or indirect, that does not involve hydrogen bonding to support-bound polynucleotides.

The tag moiety has a basic structure as shown below:

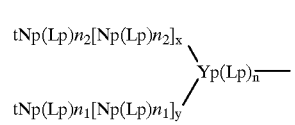

1 where Lp is a spacing monomer, Np is an internal monomer providing an attachment site for a label, tNp (terminal Np) is an internal monomer as previously defined br a monovalent 5' amino-modifer, and Yp is a bi-branching monomer. Independently, n is from about 0 to 20, usually from about 1 to 10, $n_1$ is from about 0 to 20, usually from about 1 to 10, $n_2$ is from about 0 to 20, usually from about 1 to 10, x is from about 0 to 9, and y is from about 0 to 9. One or more of the basic structures may be incorporated into the tag.

For clarity, the reactants used to produce the tag moiety are herein referred to generically as reactant monomers, and specifically as reactant-Np, reactant Lp, reactant-Yp, etc. The reactant monomers will typically have at least one phosphoramidite group, and at least one protected group suitable for chain extension, e.g. DMT or levulinyl protected hydroxyl groups. The reactant monomer may further comprise a functional group for branch elongation (reactant-Yp) or for label attachment (reactant-Np). The reactant-tNp may lack the protected group for chain extension.

Yp is a bi-branching non-nucleosidic monomer that has three functional groups for branching off each elongating chain of polymer. In one embodiment of the invention, Yp has the structure:

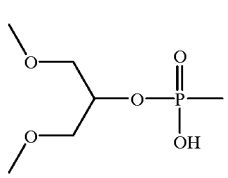

2

Reactant-Yp comprises protected hydroxyl groups at each the branch points, where the protecting group may be the same or different, in order to provide for symmetric or asymmetric branching, respectively. Reactant Yp has the general structure:

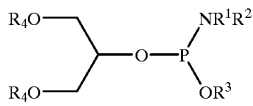

wherein $R^1$ and $R^2$ are independently chosen from hydrogen and lower alkyl, $R^3$ is β-cyanoethyl or methyl, and $R^4$ is a protecting group for a primary hydroxyl group.

Np is an attachment site monomer that provides a functional group suitable for post-synthetic attachment of a label. The functional group providing an attachment site is compatible with phosphoramidite synthesis. Groups of particular interest are amino groups, e.g. Uni-Link amino modifier, LCA-phosphoramidite, etc. Reactant-Np comprises an attachment site group and a protected group for chain extension. Reactant-tNp comprises only an attachment site group.

Examples of suitable reactant-tNp compounds include:

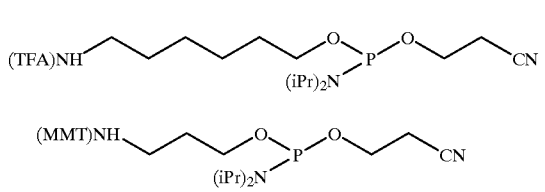

It is preferred that both Np and tNP provide an amino group.

Lp is a spacing non-nucleoside monomer. The reactant-Lp comprises two or more functional groups, two of which are needed and utilized for elongating the chain of the polymer. In one embodiment of the invention, Lp has the structure:

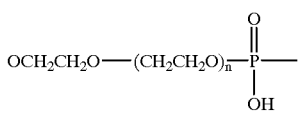

where n is 0 or 1.
Reactant Lp has the general structure:

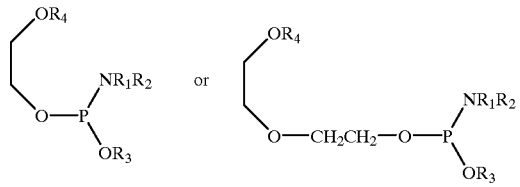

wherein $R_1$ and $R_2$ are independently chosen from hydrogen and lower alkyl, $R_3$ is β-cyanoethyl or methyl, and $R_4$ is a protecting group for a primary hydroxyl group.

A label as used herein refers to a detectable moiety, which may be a direct or indirect signal generating compounds. Suitable labels include fluorochromes, e.g. acridinium esters (AE), fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; light generating enzyme molecules, e.g. alkaline phosphatase on the stable dioxetane systems, etc. The label may be a two stage system, where the amplified DNA is conjugated to a binding compound, e.g. biotin, haptens, etc. having a high affinity binding partner, e.g. avidin, specific antibodies, etc., where the binding partner in turn carries or is covalently linked to direct signal generating molecules. The label may also provide a specific cleavage site, e.g., an enzymatic cleavage site.

Labels are attached to the tag moiety through the reactive groups provided by Np monomers. Generally a labeled probe will comprise multiple labels, ranging from at least about 5 label moieties to as much as 100 or more label moieties.

DISCLOSURE OF THE INVENTION

In a first embodiment, the invention provides a probe, comprising a nucleic acid moiety; and at least one tag moiety, wherein said tag moiety has the structure:

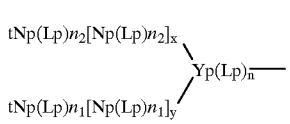

where Lp is a spacing monomer, Np is an internal monomer providing an attachment site for a label, tNp is an internal monomer as previously defined or a monovalent 5' amino-modifier, and Yp is a bi-branching monomer, independently, n is from 0 to 20, $n_1$ is from 0 to 20, $n_2$ is from about 0 to 20, x is from 0 to 9, and y is from 0 to 9.

The tags of the nucleic acid probes are highly hydrophilic non-nucleosidic moieties that include multiple labels. The tags are branched structures having a phosphodiester backbone, which are synthesized using solid phase phosphoramidite chemistry, generally in combination with synthesis of the nucleic acid portion of the probe. The tag structure permits introduction of multiple labels, while enhancing the hydrophilicity of the probes through additional phosphodiester moieties.

The nucleic acid moiety of probes is conventional, utilizing any of a number of oligonucleotide chemistries as known in the art. The specific sequence, length, complexity and degeneracy of the nucleotide sequence may vary according to the specific intended use. Probes are labeled with any of a variety of detectable compounds, particularly fluorochromes and high affinity binding moieties, e.g. avidin, digoxigenin, etc.

An example of a branched non-nucleosidic tag has the structure:

6

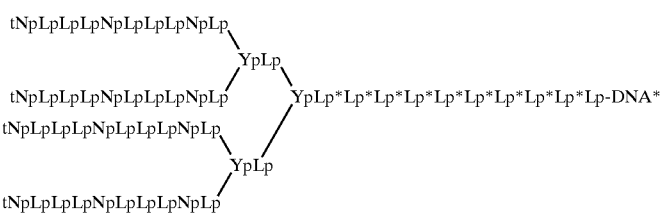

The monomers of the subject compounds serve at least two functions in the tag, one as a negative charge unit and the other as a spacing unit, in addition to the branching and label attachment functions. In structure 6, Lp* represents a tri-ethylene glycol unit introduced as its DMT protected phosphoramite, Lp represents a mono- or di-ethylene glycol unit introduced as compounds 8 and 9 below, Yp represents a bi-branching monomer introduced as compound 7, and Np represents any reagents to introduce a free amine on to the carrier for label attachment. This branched structure is shown in the orientation from 5' to 3'. If the branched carrier needs to be at the 3' end of a DNA sequence, 5' to 3' DNA synthesis chemistry should be employed (reagents available from Glen Research, Sterling, Va.; see Science (1988) 241:551–557 for method).

Two examples of 6 were synthesized using Np of Uni-Link AminoModifier (Example 6), and Np of LCA phosphoramidite (Example 8). The subject tag compounds allow an amine group, and therefore a label attachment site, to be introduced at any position in the sequence, in order to facilitate the multiplicity of labels.

The reactant monomers for synthesis of the branched tag 6 have been synthesized, or are commercially available. Reactant monomers typically have at least one phosphoramidite group and at least one protected group hydroxyl for chain elongation. The reactant monomer may further comprise a second protected hydroxyl for branch synthesis, or a functional group for label attachment.

Three reactant monomer compounds have been synthesized, with the following structures. An exemplary reactant Yp has the structure:

7

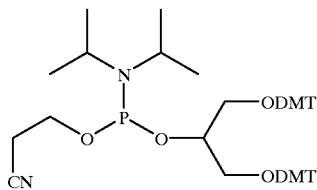

Exemplary reactant monomers for Lp have structures as shown below:

8

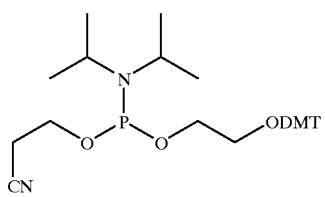

-continued

9

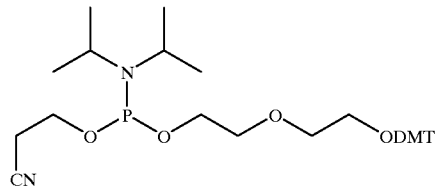

Synthesis of the non-nucleosidic branched tag uses the same reaction chemistry as phoramidite synthesis of oligonucleotides. A reactive phosphorous group of one monomer is coupled to the 5' hydroxyl of another monomer. Generally the tag will be synthesized as an extension of a glass coupled nucleic acid moiety. Acetonitrile is used as a washing solvent and the entire synthesis is performed under argon gas.

The hydroxyl group on the initial glass coupled moiety is protected by a dimethoxytrityl group (DMT). The DMT group is removed with a protic acid, such as trichloroacetic, revealing the reactive hydroxyl. As with polynucleotide synthesis, the released DMT ion is strongly colored and can easily be quantified by colorimetry or conductivity. The monomer for coupling is added with tetrazole to protonate the nitrogen of the phosphoramidite, making it susceptible to nucleophilic attack. Typically the reactive monomers will be synthesized as cyanoethyl phosphoramidites, Unlike oligonucleotide synthesis, a capping step for failure sequences, which remain uncoupled after reaction, is optional, because deletion of a single monomer will not necessarily affect the tag function in a substantial way. If it is performed, capping may be accomplished by acetylation with acetic anhydride and 1-methylimidizole. The coupled phosphite chain is then oxidized, e.g. with iodine as oxidizer and water as the oxygen donor to change the trivalent phosphoramidite to a pentavalent phosphate triester. At the end of synthesis, the finished probe is cleaved from the solid support with a strong base, e.g. ammonia. Following synthesis, the attachment groups are deprotected, if necessary, and used for label attachment with methods as known in the art.

For compound 7, with two bulky flanking DMT protective groups present, the coupling to a free hydroxy group is slow. However, by using double coupling of 10 min. each, the coupling yield reaches 88.5% to 94.5%, leaving its amplification factor of 1.77 to 1.89 (theoretical maximum of 2.0). Similarly with reactant 8, having a short distance between the DMT group and phosphorus, the coupling reaction is also slow. Using double coupling of 10 min each, the coupling yield reaches 96.7 to 100%. For compound 9, the coupling yield is always near quantitative as the regular DNA synthesis phosphoramidite reagents.

It has been previously postulated that 7 undergoes internal cyclization, however, the high coupling yields indicate that the internal cyclization is not a significant factor. In the synthesis of compound 10 below, the average stepwise coupling yield was 98.1% by manual trityl colorimetric measurement, after 30 units of compound 8 (MEG) and 10 units of a long chain amine(LCA) were introduced.

$$DNA\text{-}(MEG_3\text{-}LCA)_{10}\text{-}T \qquad 10$$

The probes of the subject invention are used in hybridization reactions and assays where a highly labeled probe is desirable. A sample potentially comprising a target nucleic acid is analyzed by one of a number of methods known in the art. Hybridization with probes to Southern blots, dot blots, etc. may be performed. The hybridization pattern of probes to an array of oligonucleotide probes immobilized on a solid support may also be used as a means of detecting the presence of target sequences. For examples of arrays, see Ramsay (1998) *Nat. Biotech.* 16:40–44; Hacia et al. (1996) *Nature Genetics* 14:441–447; Lockhart et al. (1996) *Nature Biotechnol.* 14:1675–1680; and De Risi et al. (1996) *Nature Genetics* 14:457–460.

Other applications in which the present invention may find utility include in situ hybridizations, in reducing of nonspecific binding in hybridization assays and in polymerase chain reaction (PCR) assays. In situ hybridization lacks sufficient sensitivity to detect a single molecule of target analyte. In situ PCR (see, for example Bagasra et al. (1993) *J. Immunological Methods* 158:131–145) has been developed to meet this sensitivity need; however, quantitation is not as precise with the PCR method. An alternative would use the subject probes to bind the target analyte, thereby increasing the signal produced by a single hybridization event. One skilled in the art will recognize that the same strategy could be applied to blot assays, such as dot blots, Southerns, and Northerns, to reduce nonspecific hybridization and nonspecific binding of the probes to the solid supports.

Solution phase capture hybridization may take advantage of the subject probes (see for example, U.S. Pat. No. 5,681,702). Generally the assays proceed as follows. Single-stranded analyte nucleic acid is incubated under hybridization conditions with the appropriate labeled probe. The resulting product is a nucleic acid complex of the analyte polynucleotide bound to the probe. This complex may be subsequently added under hybridizing conditions to a solid phase having capture probes bound to the surface thereof; however, in a preferred embodiment, the initial incubation is carried out in the presence of the support-bound capture probes. The resulting product comprises the complex bound to the solid phase. The solid phase with bound complex is then separated from unbound materials.

In another embodiment of the invention, a cleavage assay is performed. To further reduce the non-specific binding of a tracer or signal probe complex comprising a tag with multiple labels, a gene probe assay employing release-transfer-capture steps is used. A specifically cleavable moiety is included in the construction of the capture moiety, which is then immobilized on a solid surface. After the hybridization reaction with the probe is complete, using a conventional sandwich or branched-DNA assay format, a cleavage step is introduced to release the whole complex from the solid phase, which can then be transferred in solution form to another container to be recaptured as pure desired signal. The non-specifically bound label that is left behind includes various non-specific bound probes, which stick to the surfaces of the solid phase or container wall without specific sequence hybridization. Examples of cleavable moieties include sites for enzymes that recognize nucleic acids specifically or non-specifically, e.g. restriction endonucleases, DNAses, etc., photocleavable moieties, periodate cleavage, etc.

The reactant monomers described herein are used in the synthesis of branched or linear tags, for use in producing highly labeled nucleic acid probes. The advantages are a small dimensional size and high hydrophilicity. After the tag is labeled, its high negative charge and minimal size help to keep the carriers away from DNA or RNA molecules, due to repulsion between negative charges. Non-specific intercalation and steric hindrance are therefore minimized, and the hydrophobicity, if any of reporter molecules is reduced.

EXPERIMENTAL

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXAMPLE 1

Preparation of 1,3-Di-O-(4,4'-dimethoxytrityl)-2-hydroxy propane

To a solution of glycerol (380 mg, 4.1 mmol) in dry pyridine (5.0 ml) was added portion by portion a solution of 4,4'dimethoxytritrylchloride (2.75 g, 8.1 mmol) in pyridine (12.5 ml) at room temperature. The mixture was kept stirring for about one hour, and the pyridine was distilled off and the residue was purified on silica gel column eluted with 1% triethylamine in dochloromethane to give 2.5 g of the target product.

EXAMPLE 2

Preparation of 1,3-Di-O-(4,4'-dimethoxytrityl) propane 2-N,N-diisopropyl cyanoethylphosphoramidite (7)

To a solution of di-DMT-glycerol obtained in Example 1 above (1.15 g, 1.65 mmol) in methylene chloride (10.0 ml) containing diisopropylethylmethylamine (1.0 ml) was added drop by drop β-cyanoethyl-N,N-diisopropylchlorophosphoramidite (0.60 ml, 2.53 mmol) through a syringe at 0° C. The cooling bath was then removed and the reaction mixture was kept stirring at ambient temperature for two more hours and TLC showed the reaction was complete. Concentrated sodium carbonate solution (10 ml) was added to the reaction mixture followed by addition of 50 ml more methylene chloride. The whole mixture was then washed with water twice, dried over MgSO$_4$, and purified on flash silica gel column eluted with methylene chloride/hexane/triethylamine (2:8:0.5) to provide the target product (7) as a white foam (0.92 g).

EXAMPLE 3

Preparation of 2-0-(4,4'-dimethoxytrityl)-1-hydroxy ethane

Ethylene glycol (1.90 g, 30.6 mmol) was dissolved in 20 ml of dry pyridine and to this solution was added 4,4'- dimethoxytritylchloride (2.10 g, 6.2 mmol) at room temperature. The mixture was kept stirring for one and half hours, then pyridine was distilled off and the residue was purified on silica gel column eluted with hexane-methylene chloride-triethylamine (6:2:0.4) to provide 1.7 g of the target product.

EXAMPLE 4

Preparation of 2-0-(4,41-dimethoxytrityl)ethane 1-N,N-diisopropyl cyanoethylphosphoramidite (8)

To a solution of DMT-ethylene glycol obtained in example 3 above (1.7 g, 4.67 mmol) in methylene chloride (18.0 ml) with diisopropylethylamine (2.0 ml) was added drop by drop cyanoethyl-N,N-diisopropylchlorophosphoramidite (1.20 ml, 5.3 mmol) through a syringe at 0° C. Then the cooling bath was removed and the reaction mixture was kept stirring at ambient temperature for three more hours. The whole mixture was then washed with dilute aqueous sodium carbonate twice, dried over $MgSO_4$, and purified on flash silica gel column eluted with methylene chloride/hexane/triethylamine (2:6:0.4) to provide the target product (8) as an oily liquid (1.24 g, 2.2 mmol).

EXAMPLE 5

Preparation of (4,4'-dimethoxytrityl)diethylene glycol N,N-diisopropyl cyanoethylphosphoramidite (9)

The compound 9 was prepared in the same way as described in example 3 and example 4.

EXAMPLE 6

Preparation of Oligomer with branched tag at 5' end (10)

Oligonucleotide synthesis: the oligonucleotides were synthesized on a 1 mmole scale using an ABI 392 synthesizer and phosphoramidite chemistry. The standard 1 mmole CE cycle was modified to provide 1 minute coupling wait times for the standard dA, dG, dC and dT phosphoramidites or longer coupling wait times for the other phosphoramidites, e.g. diethylene glycol and UniLink aminomodifier phosphoramidites, as specified below. The oligonucleotides were synthesized with retention of the final 5'-dimethoxy trityl (5'-DMT) group and then deprotected with ammonium hydroxide (14.8 M) at 55° C. for 15 hours. The oligonucleotides were purified by RP-HPLC (7 micron Aquapore RP-300, 7×250 mm) eluting with 8–20% acetonitrile in 0.1 M triethylammonium acetate over 20 minutes followed by 20–60% acetonitrile over an additional twenty minutes. The 5'-DMT group was removed with 80% acetic acid and the desired oligonucleotides was repurified by RP-HPLC.

The synthesis of 10 was carried out on an ABI synthesizer using routine chemistry with all the reagents concentrations at 0.10 M in dry acetonitrile. Starting from the first branching Yp through the end, double coupling with 10 minutes each was used to introduce those phosphoramidites. Reagents used are: Yp of 7, Lp of 9, Lp* of DMT protected phosphoramidite of triethylene glycol, and Np of Uni-Link AminoModifier (ClonTech).

EXAMPLE 7

Preparation of Oligomer with linear tag at 3' end (10)

The synthesis of 10 was carried out also with all the reagents concentrations at 0.10 M in dry acetonitrile. The 3' tail was synthesized using double coupling with 10 minutes each, until the regular DNA sequence starts. Reagents used are: Lp of 2, Np of LCA phosphoramidite.

EXAMPLE 8

Preparation of Oligomer with branched tag at 5' end (11)

The synthesis of 10 was carried out on an ABI synthesizer using the routine chemistry with all the reagents concentrations at 0.10 M in dry acetonitrile. Starting from the first branching Yp through the end, double coupling with 10 minutes each was used to introduce those phosphoramidites. Reagents used are: Yp of 7, Lp of 8, Lp* of DMT protected phosphoramidite of triethylene glycol, and Np of LCA phosphoramidite. The structure of this product is as follows:

(11)

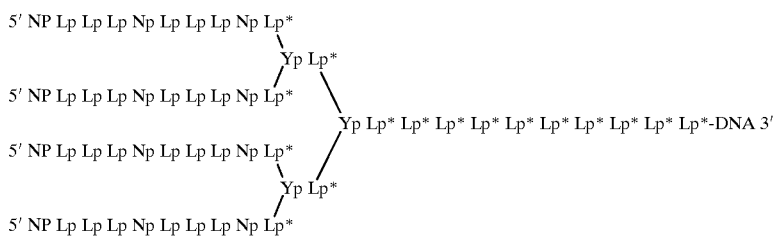

EXAMPLE 9

Preparation of of BLA3 probe labeled with single acridinium ester (DMAE)

BLA3 probe with primary amine group at the 3'-end (AAG TAC GAC AAC CAC ATC T-NH2). The oligomer was synthesized starting with 3'-Amino-Modifier C7 CPG (Catalog #20-295741, Glenn Research, Sterling, Va.) on a ABI synthesizer as described before.

LA3-AE conjugate: To a 4 ml vial containing a micro stir bar was added $3.5 \times 10^{-8}$ moles of BLA3-NH$_2$ in 200 µl of 0.1 M NaHCO$_3$ (pH 8.5). To the oligonucleotide solution was added 100 µl of dimethylformamide (DMF) followed by 0.67 milligrams of 2',6'-dimethyl-4'-(N succinidyloxycarbonyl) phenyl- 10-methyl-acridinium-9-carboxylate methyl sulfate (DMAENHS) in 33 µl of DNW. The reaction was purged with nitrogen and allowed to stir at room temperature. After 1 hour an additional 0.67 milligrams of DMAE-NHS in 33 µl of DMF was added with continued stirring. After 1 hour a third addition of 0.67 milligrams of DMAE-NHS in 33 µl of DMF was added and the reaction was stirred for 15 hours. The reaction contents were then purified on Sephadex G-25 (Fine, 1.5×40 cm) eluting with 0.01 M $KH_2PO_4$ pH 7.0. The initial $A_{260}$ absorbing material was collected, lyophilized and further purified by RP-HPLC (7 micron Aquapore RP-300, 7×250 mm) eluting with 8–20% acetonitrile in triethylammonium acetate over 20 minutes followed by 20–60% acetonitrile over an additional twenty minutes. The product eluting at $R_t$=26.1 minutes was collected and lyophilized. The AE labeled oligonucleotide was redissolved in 1- water and was quantified by its absorbance at 260 nm ($7.0 \times 10^{-9}$ moles) and the DMAE *>content was quantified by the relative light unit count ($7.0 \times 10^{-9}$ moles) on a luminometer, MLA-1 (Ciba Coming Diagnostics, Medfield, Mass.) equipped with a BG-12 optical filter.

EXAMPLE 10

Preparation of BLA3 probe labeled with 4 acridinium esters

BLA3 probe tailed with mixed diethylene glycol and Aliphatic Unilink Amino Modifier phosphodiester repeats [BLA3-$(X_5U)_4AT$]:

X=diethylene glycol
U=Uni-Link™ amino modifier (Catalog #5190-2, Clontech Laboratories, Palo Alto, Calif.).

The oligonucleotide was synthesized on a 1 mmole scale as described above. The standard 1 mmole CE cycle was modified to provide 1 minute coupling wait times for the standard dA, dG, dC and T phosphoramidites and 2 minute coupling wait times for the diethylene glycol and UniLink aminomodifier phosphoramidites.

BLA3-$(X_5U)_4AT$ labeled with 4 acridinium esters. To a 4 ml vial containing a micro stir bar was added $2 \times 10^{-8}$ moles of BLA3-$(X_5U)_4AT$ in 200 µl of 0.1 M $NaHCO_3$ (pH 8.5). To the oligonucleotide solution was added 100 µl of dimethylformamide (DMF) followed by 0.67 milligrams of 2', 6'-dimethyl-4'-(N-succinimidyloxycarbonyl) phenyl-10-methyl-acridinium-9-carboxylate methyl sulfate (DMAE-NHS) in 33 µl of DMF. The reaction was purged with nitrogen and allowed to stir at room temperature. After 1 hour an additional 0.67 milligrams of DMAE-NHS in 33 uL of DMF was added with continued stirring. After 1 hour a third addition of 0.67 milligrams of DMAE-N-HS in 33 µl of DMF was added and the reaction was stirred for 15 hours. The reaction contents were then purified on Sephadex G-25 (Fine, 1.5×40 cm) eluting with 0.01 M $KH_2PO_4$ pH 7.0. The initial $A_{260}$ absorbing material was collected, lyophilized and further purified by RP-HPLC (7 micron Aquapore RP-300, 7×250 mm) eluting with 8–20% acetonitrile in triethylammonium acetate over 20 minutes followed by 20–60% acetonitrile over an additional twenty minutes. The product eluting at $R_t$=29.7 minutes was collected and lyophilized. The AE labeled oligonucleotide was redissolved in water and was quantified by its absorbance at 260 nm ($3.33 \times 10^{-9}$ moles) and the DMAE content was quantified by the relative light unit count ($13.6 \times 10^{-9}$ moles) on a luminometer, MLA-1 equipped with a BG-12 optical filter.

EXAMPLE 11

Greater Gene Probe Assay Sensitivity Achieved Using Probes with Multiple Acridinium Ester Labels The purpose of the experiment was to compare the sensitivity of the single and multiple Acridinium Ester (AE) labeled detection probes to the reference alkaline phosphatase labeled detection probe using the branched DNA (bDNA) signal amplification method. The Quantiplex™ HIV-RNA bDNA assay (Chiron Corp., Emeryville Calif.) was used.

The Quantiplex™ HIV assay is based on the specific hybridization of synthetic oligonucleotides to the HIV-1 pol gene, which allows the RNA to be captured onto the surface of a well in a microtiter plate format. Synthetic branched DNA molecules (bDNA) and multiple copies of an alkaline phosphatase conjugated detection probe are hybridized to the immobilized complex (signal amplification). In the Quantiplex™ assay detection is achieved by incubating the complex with a chemiluminescent substrate and measuring the light emission generated by the bound alkaline phosphatase.

In this example, either one or four acridinium esters were conjugated to the detection probe in place of the alkaline phosphatase. Detection was achieved by removing the bound AE at the end of the assay, oxidizing the AE with alkaline hydrogen peroxide and measuring the light emission in a Ciba Coming Diagnostic MLAII Luminometer (Ciba Coming Diagnostics, Medfield Mass.).

HIV Target Preparation: RNA was prepared by T7 RNA polymerase transcription of a linearized recombinant plasmid containing a 2.8 Kb HIV-I insert. The RNA transcripts were prepared using a T7 MAXIscript™ Kit (Ambion, Austin Tex.) and the yield determined by either incorporation of α-$^{32}$P-UTP or by optical density ($A_{260}$). Single stranded M13 Phage DNA carrying the same 2.8 kb HIV-1 insert was also used in the assay.

bDNA Assay: The experiment utilized the Chiron Quantiplex™ HIV type-1 RNA kit according to the manufacturer's instructions. Detection of the bound alkaline phosphatase detection probe is accomplished by incubation with a chemiluminescent substrate for 30 minutes at 37° C. in the microtiter plate well. The steady state "glow" of light is measured with the Q2000 luminometer (Chiron Corp., Emeryville Calif.).

The bDNA assays with AE detection probes were modified by the substitution of the acridinium ester conjugate in place of the alkaline phosphatase (AP). The specifically bound AE detection probe is removed from the microtiter well with DNase 1 (30 minutes at 37° C.) and transferred to a 12×75 mm test tube compatible with the Ciba Coming Diagnostic MLAII Luminometer. The acridinium ester labeled probe was detected by the sequential addition on the instrument of hydrogen peroxide in dilute nitric acid (Flash reagent 1) followed by the addition of sodium hydroxide and Arquad™, Akzo Nobel, Chicago, Ill. (Flash reagent 2). The chemiluminescent "flash" of light is collected for two seconds.

The tube transfer step was needed for the detection of AE because the microtiter wells would not fit into the available MLAII Luminometer. Additionally, it serves to leave behind the nonspecifically bound AE detection probes, as shown by the comparable low backgrounds of the negative controls after tube transfer, regardless whether 1-AE or 4-AE probes were added. Microtiter plate readers compatible with AE based chemiluminescent detection are commercially available.

Both of the luminometers used in this example report signal as relative light units (RLU), however, one relative light unit (RLU) on the Q2000 is equivalent to 1000 relative light units (RLU) on the Ciba Coming Diagnostic MLAII Luminometer.

Results: The signal in the AE Assay is improved four fold when a detection probe containing four AE molecules was used. The two tables below show the results of one experiment. Each data point is the mean of four data points. The data points are expressed as relative light units (RLUs) and are background corrected. The comparison of a single AE label probe (AE-1) versus the multiple AE probe (AE-4) with a phage single stranded DNA target is shown in Table 1.

TABLE 1

Net RLU with a DNA Target

| # of molecules | AP (Q2000 - RLU) | AE-I (MLA - RLU) | AE-4 (MLA - RLU) |
| --- | --- | --- | --- |
| 3,200,000 | 3,766 | 3,077 | 13,950 |
| 400,000 | 476 | 489 | 2,001 |
| 80,000 | 106 | 75 | 521 |
| 20,000 | 41 | 44 | 236 |

The comparison of a single AE label probe (AE-1) versus the multiple AE probe (AE-4) with an RNA target is shown in Table 2.

TABLE 2

Net RLU with a RNA Target

| # of molecules | AP (Q2000 - RLU) | AE-I (MLA - RLU) | AE-4 (MLA - RLU) |
| --- | --- | --- | --- |
| 10,000,000 | 6,458 | 6,652 | 24,955 |
| 1,000,000 | 852 | 920 | 5,790 |
| 100,000 | 81 | 129 | 623 |
| 10,000 | 25 | 49 | 134 |

The results obtained with the alkaline phosphatase labeled detection were consistent with performance expected for the Quantiplex™ HIV assay. The assay easily detected the lowest level of target used. The signal observed in the absence of target was 12 RLU. This signal is approximately fifty times the background with the chemiluminescent substrate alone. In the above tables the net signal is shown (Net RLU=Total RLU-RLU in the absence of target). The results obtained with the AE labeled detection probes are also reported as net signal, however the RLUs observed in the absence of target (645 RLU with I AE and 671 RLU with 4AEs) was equivalent to the instrument background alone. Hence, adding four times more label (with 4AEs per detection probe) did not result in a higher background. This result was consistent with the design of the experiment which utilized a tube transfer step. At the lowest target number the signal is near the instrument background in assays with the AE detection probes and hence, signal is limiting. The level of detection and therefore sensitivity for the AE assay, while not as sensitive as the AP assay, is improved by using the multiple AE detector probe.

Conclusion: the signal in the Quantiplex™ HIV-RNA which used a detection probe containing four acridinium esters was four times higher than the detection probe which contained only one acridinium ester. This improved signal results in a more sensitive assay.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. A probe, comprising:

a nucleic acid moiety; and at least one tag moiety, wherein said tag moiety has the structure:

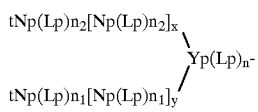

where Lp is a spacing monomer, Np is an internal monomer providing an attachment site for a label, tNp is an internal monomer at a terminal position providing an attachment site for a label or a monovalent 5' amino-modifier, and Yp is a bi-branching monomer comprising the structure

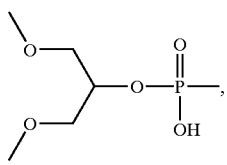

and where independently, n is from 0 to 20, $n_1$ is from 0 to 20, $n_2$ is from about 0 to 20, x is from 0 to 9, and y is from 0 to 9.

2. The probe of claim 1, comprising two or more tag moieties.

3. The probe of claim 1, wherein both Np and tNp provide an amino group.

4. The probe of claim 1, wherein Lp has the structure:

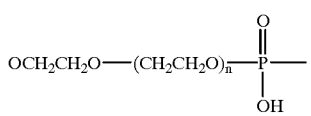

where n is 0 or 1.

5. The probe of claim 3, further comprising one or more label(s) attached to said amino group(s).

6. The probe of claim 5, wherein said label is a detectable compound.

7. The probe of claim 5, wherein said label is a binding compound.

8. The probe of claim 5, wherein said label provides a specific cleavage site.

9. The probe of claim 1, wherein said nucleic acid is a synthetic single-stranded oligonucleotide with or without branched segment, that is capable of hybridizing to a single-stranded nucleic acid of interest under hybridizing conditions.

* * * * *

UNITED STATES PATENT AND TRADEMARK OFFICE
CERTIFICATE OF CORRECTION

PATENT NO.    : 6,504,019 B2                                              Page 1 of 1
DATED         : January 7, 2003
INVENTOR(S)   : Guohan Yang et al.

It is certified that error appears in the above-identified patent and that said Letters Patent is hereby corrected as shown below:

<u>Column 16,</u>
Line 62, please delete "is capable of hybridizing" and replace with -- hybridizes --.

Signed and Sealed this

Twenty-fourth Day of June, 2003

JAMES E. ROGAN
*Director of the United States Patent and Trademark Office*